(12) United States Patent
Hardy et al.

(10) Patent No.: US 11,617,685 B2
(45) Date of Patent: Apr. 4, 2023

(54) WOUND DRESSING

(71) Applicant: MEDTRADE PRODUCTS LIMITED, Crewe (GB)

(72) Inventors: Craig Hardy, Cardigan (GB); Andrew Hoggarth, Crewe (GB); David Warde, Manchester (GB)

(73) Assignee: MEDTRADE PRODUCTS LIMITED, Cheshire (GB)

( * ) Notice: Subject to any disclaimer, the term of this patent is extended or adjusted under 35 U.S.C. 154(b) by 230 days.

(21) Appl. No.: 15/127,395

(22) PCT Filed: Mar. 19, 2015

(86) PCT No.: PCT/GB2015/050815
§ 371 (c)(1),
(2) Date: Sep. 19, 2016

(87) PCT Pub. No.: WO2015/140563
PCT Pub. Date: Sep. 24, 2015

(65) Prior Publication Data
US 2018/0168870 A1 Jun. 21, 2018

(30) Foreign Application Priority Data
Mar. 19, 2014 (GB) ..................................... 1404954

(51) Int. Cl.
| | | |
|---|---|---|
| A61F 13/02 | (2006.01) | |
| A61L 15/22 | (2006.01) | |
| A61L 15/28 | (2006.01) | |
| A61L 15/48 | (2006.01) | |
| A61L 15/60 | (2006.01) | |
| A61F 13/00 | (2006.01) | |
| A61L 26/00 | (2006.01) | |

(52) U.S. Cl.
CPC .... *A61F 13/0213* (2013.01); *A61F 13/00008* (2013.01); *A61F 13/00012* (2013.01); *A61F 13/00017* (2013.01); *A61L 15/225* (2013.01); *A61L 15/28* (2013.01); *A61L 15/48* (2013.01); *A61L 15/60* (2013.01); *A61L 26/009* (2013.01); *A61L 26/0023* (2013.01); *A61L 26/0052* (2013.01); *A61L 26/008* (2013.01)

(58) Field of Classification Search
None
See application file for complete search history.

(56) References Cited

U.S. PATENT DOCUMENTS

| | | | |
|---|---|---|---|
| 2004/0028739 A1 | 2/2004 | Rippon et al. | |
| 2005/0064021 A1 | 3/2005 | Rippon et al. | |
| 2005/0137272 A1* | 6/2005 | Gaserod | C08L 5/04 521/50 |
| 2012/0149659 A1* | 6/2012 | Haggard | A61L 29/16 514/55 |

FOREIGN PATENT DOCUMENTS

| | | |
|---|---|---|
| GB | 2463523 A | 3/2010 |
| WO | 01/24840 A1 | 4/2001 |
| WO | 2007/074327 A1 | 7/2007 |
| WO | 2010/031995 A2 | 3/2010 |
| WO | 2014/072721 A1 | 5/2014 |

OTHER PUBLICATIONS

Alexandridis et al., "Poly(ethylene oxide)-poly(propylene oxide)-poly(ethylene oxide) block copolymer surfactants in aqueous solutions and at interfaces: thermodynamics, structure, dynamics, and modeling", 1995, Colloids and Surfaces, vol. 96, pp. 1-46.*
Vikhoreva et al., "Modification of Chitosan Films with Surfactants to Regulate their Solubility and Swelling", Fibre Chemistry, vol. 30, No. 1, 1998, pp. 14-19.*
International Search Report for PCT Application No. PCT/GB2015/050815 dated Jun. 18, 2015.
United Kingdom Search Report for application No. GB1404954.8 dated Sep. 20, 2014.

* cited by examiner

*Primary Examiner* — Robert A Wax
*Assistant Examiner* — Randeep Singh
(74) *Attorney, Agent, or Firm* — Tarolli, Sundheim, Covell & Tummino LLP

(57) ABSTRACT

The present invention relates to a wound dressing composition that is capable of gelling upon contact with a fluid derived from a human or animal body, and which is able to maintain the integrity of the gel for a period of time that is longer than about 24 hours.

24 Claims, No Drawings

WOUND DRESSING

RELATED APPLICATIONS

The present invention is a U.S. National Stage under 35 USC 371 patent application, claiming priority to Serial No. PCT/GB2015/050815, filed on 19 Mar. 2015; which claims priority from 1404954.8, filed 19 Mar. 2014, the entirety of both of which are incorporated herein by reference.

TECHNICAL FIELD

The present invention relates to a wound dressing composition that is capable of gelling upon contact with a fluid derived from a human or animal body, and which is able to maintain the integrity of the gel for a period of time that is longer than about 24 hours.

BACKGROUND

Wound dressing materials for use in the treatment of wounds or other openings at a physiological target site in or on human or animal body which are exuding blood and/or other bodily fluids have been known for some time. These wound dressing materials act to absorb the blood and/or other bodily fluids, and also stem the flow of them from the body. Wound dressing materials for such use are described in, for example, WO2010031995 to MedTrade Products Ltd., and are commercially available.

The management of exudate is of course essential and critical during wound care and surgical procedures. The aim of managing the exudate is essentially to provide a moist wound environment at the wound bed and minimise the risk of maceration, which in turn may reduce the negative impact upon the human or animal body and also shorten the length of time the patient will take to recover.

One material that is reported to have a use in wound healing is chitosan. Chitosan is a known haemostat for use in wound dressing materials, and is a derivative of solid waste from shellfish processing and can be extracted from fungus culture. It is a cationic polymeric material that is insoluble in water.

There are many different types of chitosan that may be used as a wound dressing material, with different wound dressing and absorption properties. The different types of chitosan may have different molecular weights, different degrees of deacetylation, different arrangements of the two monomers, different chiral forms, or they may be derived from different species or sources (and fungi), or may have been treated differently during manufacture. Each and all of these different variations of chitosan materials are envisaged for use within the present invention.

Chitosan materials that exhibit gelling properties upon contact with fluid from a human or animal body typically consist of chitosan, which may be in a fibrous form, for example, and lactic acid. However, when these chitosan fibres are immersed in simulated wound fluid and lysozyme solution, the fibres do indeed gel, but within a period of less than 24 hours, the fibres lose their fluid retention ability, which causes the gel to collapse. It is believed that this collapse is attributable to degradation of the gel structure by enzymes in the bodily fluid.

Clearly, this degradation is undesirable for wound dressings, as the collapse of the gel results in a lower fluid retention by the wound dressings, which may potentially lead to wound maceration as the patient's wound and skin is exposed to fluids that have leaked from the gel as it degrades as well as fluids that are exuded from the body.

There therefore remains a need for a wound dressing composition that is able to maintain its gel integrity and gel structure for a longer period of time than existing wound dressing compositions, but which will still break down after a desired period of time to permit a wound to heal. Such a wound dressing composition has never previously been developed.

SUMMARY

Therefore, in accordance with the invention, there is provided a wound dressing composition comprising a chitosan, chitosan salt or chitosan derivative, wherein the wound dressing composition forms a gel upon contact with a fluid from a human or animal body, and is able to maintain gel integrity for at least about 24 hours.

Typically, the wound dressing composition comprises a chitosan salt.

By 'gel integrity' is meant herein that the fluid retention of the wound dressing composition is at least about 70%, and more typically at least about 80%, when the wound dressing composition is under compression at a pressure of about 40 mmHg. The compression is typically applied for about 2-4 minutes, typically 3 minutes, at this pressure. This pressure level is chosen as this is generally regarded as the pressure at the ankle for compression therapy.

Also, by the wound dressing composition maintaining its 'gel integrity' is meant that the formed gel is able to conform to an uneven surface, i.e. it is able to adopt and retain the shape of any uneven surface it is applied to, in contrast to a wound dressing composition that has lost its gel integrity, which will not be able to do this due to it having a more fluid form.

Further, by the wound dressing composition maintaining its 'gel integrity' is meant that upon compression, the wound dressing composition does not dry out, i.e. the composition does not lose the fluid such that the appearance of the wound dressing composition is a dry material or fibre.

If the gel integrity of the wound dressing composition is lost, then this means that one or more of the above statements do not apply, i.e. the fluid retention upon compression is less than about 70%; the conformability of the wound dressing composition changes such that it is unable to conform to an uneven surface; and the wound dressing composition can be compressed such that it loses a sufficient amount of the fluid retained therein that it develops a dry outward appearance.

The wound dressing composition of the invention prevents this loss of gel integrity from occurring, such that upon absorption of fluids from a human or animal body, the wound dressing composition will form a gel and maintain its gel integrity as determined by the criteria defined hereinabove for a period of at least 24 hours, thus avoiding issues of wound and peri-wound skin maceration, and also avoiding the need for consequential increased changes of the wound dressing due to saturation during the initial healing period for the wound. After this period, it will then degrade and lose its integrity and display the characteristics described above for a loss of gel integrity.

Typically, the wound dressing of the invention is able to maintain its gel integrity over a period of about 48 hours, 72 hours, 4 days, 5 days, 6 days, or even over a minimum of about 7 days. The wound dressing of the invention may even be able to maintain its gel integrity over a period of about 14 or 21 days. Of course, the duration of the gel integrity will be dependent on the level of exudate from the physiological target site.

By "Wound Dressing", it is meant herein any agent which is capable of forming a gel when it comes into contact with blood or other bodily fluid from a physiological target site of a human or animal body.

By "Haemostat", it is meant herein any agent which is capable of producing a clot or plug which stops or reduces bleeding when it comes into contact with blood or other bodily fluid from a physiological target site of a human or animal.

The physiological target site may be any site in the body of an animal that is exposed due a wound or during a surgical procedure. The animal may be a human or a non-human animal.

By the term 'chitosan derivative' is meant herein a partially deacetylated chitin, which may have different percentages of deacetylation, as desired. Typically, the partially deacetylated chitin suitable for use in the present invention has a deacetylation degree above about 50%, more typically above about 75% and most typically above about 85%.

Also herein included within the term 'chitosan derivative' are reaction products of chitosan with other compounds. Such reaction products include, but are not limited to, carboxymethyl chitosan, hydroxyl butyl chitin, N-acyl chitosan, O-acyl chitosan, N-alkyl chitosan, O-alkyl chitosan, N-alkylidene chitosan, O-sulfonyl chitosan, sulfated chitosan, phosphorylated chitosan, nitrated chitosan, alkalichitin, alkalichitosan, or metal chelates with chitosan, etc.

The chitosan, chitosan salt or chitosan derivative may be in any form, such as fibres, granules, powder, a sheet, a foam, a freeze dried foam, a compressed foam, a film, a perforated film, beads; however, the chitosan, chitosan salt or chitosan derivative is typically in the form of fibres.

Typically, the wound dressing of the invention is in a fibrous form, such as in the form of a nonwoven which is structurally capable of being applied to the wound and removed in one piece. Alternatively, it is also possible to coat a wound surface with granules that gel and maintain their gel integrity. It is also feasible to manufacture a dry sheet that gels on contact with fluid (like a sheet hydrogel), that maintains its gel integrity.

The wound dressing composition of the invention typically also contains an anionic surfactant. In addition, the wound dressing composition of the invention may also comprise a copolymer comprising two or more homopolymer sub-units linked by covalent bonds. Of course, both the anionic surfactant and poloxamer must be physiologically acceptable to a human or animal.

The anionic surfactant cross-links the chitosan and inactivates lysozyme activity, while the poloxamer is used also to inactivate lysozyme activity, as well as a wetting agent. The deactivation of the lysozyme retards the degradation of the gel by the enzyme.

Examples of anionic surfactants that may be used in the present invention include, but are not limited to, sodium dodecyl sulphate (SDS), ammonium lauryl sulphate, dioctyl sodium sulfosuccinate, potassium lauryl sulphate, sodium dodecylbenzenesulfonate, sodium laureth sulphate, sodium lauroyl sarcosinate, sodium myreth sulphate, sodium pareth sulphate, sodium stearate, and combinations of any two or more thereof. Typically, the anionic surfactant comprises, or is, sodium dodecyl sulphate.

The anionic surfactant is typically present in an amount of between about 0.01% to about 10.00% by weight of the wound dressing composition. More typically, the anionic surfactant is present in an amount of between about 1.00% to about 5.00%, more typically between about 1.50% to about 3.00%.

According to an embodiment of the invention, the copolymer comprising two or more homopolymer sub-units linked by covalent bonds contain an approximate molecular mass of poly(propylene oxide) of from between 100 g/mol and 400 g/mol with a percentage poly(ethylene oxide) content of from about 10% to about 80%, more preferably an approximate molecular mass of the poly(propylene oxide) of from between 150 g/mol and 250 g/mol with a percentage poly(ethylene oxide) content of from about 50% to about 80%.

Typically, the copolymer comprising two or more homopolymer sub-units linked by covalent bonds is a poloxamer. Poloxamers are nonionic triblock copolymer composed of a central hydrophobic chain of poly(propylene oxide) flanked by two hydrophilic chains of poly(ethylene oxide). Commercially available poloxamers are known, for example, under the trade names Synperonics, Pluronics, and Kolliphor. Because the lengths of the polymer blocks can be customized, many different poloxamers exist that can have slightly different properties.

Examples of poloxamers that may be used in the present invention include, but are not limited to, Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, and combinations of any two or more thereof. Poloxamer 188 is a typically used poloxamer.

Because the lengths of the polymer blocks can be customized, many different poloxamers exist, which have slightly different properties. The accepted nomenclature of poloxamers in the art is that these copolymers are commonly are prefixed with the letter 'P'—for 'Poloxamer'—followed by three digits. The first two digits multiplied by a factor of 100 gives the approximate molecular mass of the polyoxypropylene core, and the last digit multiplied by a factor of 10 gives the percentage polyoxyethylene content of the copolymer.

The copolymer comprising two or more homopolymer sub-units linked by covalent bonds, such as a poloxamer, is typically present in an amount of between about 0.01% to about 5.00% by weight of the wound dressing composition. More typically, the copolymer is present in an amount of between about 1.00% and 3.00%, still more typically between about 1.50% and about 2.50%, most typically about 2.0%.

According to one embodiment of the invention, the wound dressing composition may also contain a physiologically acceptable acid. Examples of acids that may be used include, but are not limited to, organic acids and/or inorganic acids, including carboxylic acids, monovalent, divalent or multivalent acids. Non-limiting examples of carboxylic acids include formic acid, acetic acid, ascorbic acid, halogen acetic acids (such as fluoro- or chloroacetic acid), propanoic acid, propenoic acid, lactic acid, succinic acid, acrylic acid, glyoxylic acid, pyruvic acid or a hydroxy propionic/butanoic acid, or combinations of any two or more thereof. More typically, the carboxylic acids used are one or more acids selected from lactic, acetic and succinic acids. Most typically, the carboxylic acid used comprises lactic and/or acetic acids, especially lactic acid. Non-limiting examples of inorganic acids include one or more selected from hydrochloric acid and sulphuric acid. The use of an acid which is already present in the human or animal body is advantageous in facilitating the bioacceptability of the wound dressing composition as it degrades.

The physiologically acceptable acid is typically present in an amount of between about 15% to about 55% by weight of the wound dressing composition. More typically, the acid is present in an amount of between about 20 to about 50%, or between about 22 to about 40%, or more typically between about 25 to about 30% by weight of the wound dressing composition. If levels of acid below 15% are used, the gel 'collapses' within 24 hours, e.g. the material changes from a gel presentation to a fabric, which is associated with an insufficient level of fluid retention (<70%).

The wound dressing composition of the invention works effectively at normal body temperatures (37° C.).

It will be appreciated that the amount of surfactant, copolymer and physiologically acceptable acid that may be present in the wound dressing composition can significantly impact upon the degradation properties of the composition, and also that the optimum amount of the surfactant, copolymer and physiologically acceptable acid for the desired degradation properties may vary with different specific compounds thereof, and also with different grades of chitosan (e.g. having differing molecular weights and/or degrees of deacetylation). The optimum amount of surfactant, copolymer and physiologically acceptable acid required for the desired degradation properties may also differ depending upon the form of the chitosan wound dressing, among other factors.

According to one embodiment of the invention, there is provided a wound dressing composition comprising chitosan, chitosan salt or chitosan derivative, an anionic surfactant and a poloxamer. This composition may also contain an amount of a physiologically acceptable acid.

According to one embodiment of the invention, the wound dressing composition comprises chitosan in the form of fibres, lactic acid, sodium dodecyl sulphate, and a poloxamer comprising a block copolymer comprising units of poly(ethylene oxide) and poly(propylene oxide), such as Pluronic F68 (Poloxamer 188).

According to one embodiment of the invention, the wound dressing composition is a chitosan salt. If a chitosan salt is used, the salt is typically prepared in situ when the chitosan comes into contact with an appropriate physiologically acceptable acid. It will be appreciated that the acid may be any organic or inorganic acid which yields a chitosan salt that is soluble in bodily fluids and that can be safely degraded within the human or animal body. The appropriate acids or combination of acids for yielding a soluble chitosan salt will be apparent to a skilled person. For example, chitosan phosphate is substantially insoluble in water, and so use of phosphoric acid alone would hence be less suitable as the acid for this purpose. Typical chitosan salts include herein, but are not limited to, one or more salts selected from chitosan acetate, chitosan lactate, chitosan succinate, chitosan malate, chitosan acrylate, chitosan formate, chitosan ascorbate, chitosan fluoroacetate, chitosan chloroacetate, chitosan propanoate, chitosan glyoxylate, chitosan pyruvate, chitosan sulphate, or chitosan chloride. More typically, the chitosan salt used in the present invention is chitosan lactate.

Furthermore, chitosan salts exhibit mild antibacterial properties and as such their use reduces the risk of infection.

Typically, the molecular weight of the chitosan used for the preparation of the wound dressing composition according to the present invention is less than about 2,000,000, more typically less than about 1,000,000, and even more typically less than about 500,000, and most typically less than about 175,000.

The viscosity of the chitosan used according to the invention may typically be less than about 1000 cps, more typically less than about 500, even more typically less than about 300. Advantageously, the viscosity is from about 40 to about 200 cps when measured on a Brookfield viscometer at 20° C.

The chitosan typically has a pH of from about 6.0 to about 8.0. Chitosan salts can have a pH from about 3.5 to about 8.0. The pH is largely dependent upon the particular chitosan or chitosan salt used, as they each have a different pH.

Typically, the wound dressing composition of the invention is in fibrous form. By fibrous form is meant herein that the chitosan is composed of fibres of a desired size or sizes, and is formed into a textile fabric or a pad for use. The textile fabric or pad may be woven or non-woven.

If the wound dressing composition is provided in a fibrous form, the fibres typically have a minimum average length of about 3 mm and a maximum length of about 500 mm, more typically no more than about 76 mm. The typically preferred length of the fibres is at least 10; more preferred at least 38 and most preferred at least 51 mm.

Alternatively, the wound dressing composition of the invention may comprise nano-fibres, i.e. fibres having a diameter of no more than about 100 microns. Similarly, the length of the nano-fibres is no more than about 100 microns.

The wound dressing composition described herein provides and maintains effective absorption properties when applied to a wound requiring exudate management or a surgical opening requiring exudate management.

It is also beneficial to deliver a wound dressing composition that is able to not adhere to the body tissues, ensuring that any wound dressing product does not result in trauma on removal; the present invention is also able to fulfil this requirement.

According to one embodiment of the invention, the wound dressing composition may be applied with other physiologically safe materials, such as, for example, polyurethane foams, polyurethane films, i.e. secondary dressings. Other suitable and safe materials that may be combined with the wound dressing composition will be apparent to the person skilled in the art.

Further components which may be added to the wound dressing composition include, but are not limited to, one or more selected from pharmaceutical agents; wetting agents such as surfactants; growth factors; cytokines; agents which absorb agents which delay healing such as MMP's (matrix metalloproteinases) and elastase; and/or another wound dressing component, such as calcium, vitamin K, fibrinogen, thrombin, factor VII, factor VIII, clays such as kaolin, oxidised regenerated cellulose, gelatin, or collagen, etc.

Typical levels of any of these components could be from about 50 ppm levels up to about 50% by weight of the wound dressing composition. More typical levels would be less than about 10%, still more typically less than about 5%, by weight of the wound dressing composition. Less than about 1% by weight of the wound dressing composition of these components is also envisaged within the invention.

A further embodiment of this invention is the inclusion of other fibres or textiles through the body of the wound dressing that provide structural strength, enabling the product to be removed from the wound following saturation.

According to a further aspect of the invention, there is provided a method of manufacturing a wound dressing composition comprising a chitosan, chitosan salt or chitosan derivative, wherein the wound dressing composition forms a gel upon contact with a fluid from a human or animal body, and is able to maintain gel integrity for at least about 24 hours.

The method may typically comprise contacting the chitosan, chitosan salt or chitosan derivative with a solution comprising one or more of a physiologically acceptable acid, an anionic surfactant and/or a copolymer comprising two or more homopolymer sub-units linked by covalent bonds; typically an anionic surfactant is added, and one or both of the acid and copolymer may also be added. all three of these components are added. The physiologically acceptable acid, anionic surfactant and poloxamer may be any of those materials previously identified hereinabove. The solution may also comprise a physiologically acceptable solvent, such as but not limited to monohydric alcohols, such as isopropyl alcohol or ethanol.

The chitosan material is typically in fibrous form, and may already contain an antimicrobial agent, and/or any other further component as desired, prior to being contacted with the solution. If the chitosan material is in fibrous form, it is typically carded into a textile fabric or a pad for use, such as a non-woven textile (50-300 gsm).

The solution may typically be coated onto the chitosan, chitosan salt or chitosan derivative, using, for example, a dip batch or spray system, or any other suitable coating technique known to the skilled person. Following the contacting of the chitosan, chitosan salt or chitosan derivative with the solution, the coated chitosan material is dried.

The chitosan material may be provided in a sterile or non-sterile form. Where the material is initially provided in a sterile form, sterilisation may be carried out using any of the methods conventionally known in the art, such as gamma irradiation, electron beam treatment, heat treatment, x-ray, etc, or it may alternatively be carried by a treatment using ethylene oxide. Sterilisation using ethylene oxide is preferred. A material in a non-sterile form may be provided in combination with one or more preservatives. However, it is preferred that the wound dressing composition is provided in a pre-sterilised form.

In one embodiment, the chitosan raw material may first be washed to reduce the presence of endotoxins prior to the coating step. This may be carried out by contacting the chitosan, chitosan salt or chitosan derivative with an alkali solution to form a mixture, and then leaving the mixture for a period of time, which may be as short as about 1 minute to longer than about 12 hours, before finally drying the mixture. By 'alkali solution' is meant a solution having a pH value of greater than pH 7.5.

The concentration of alkali solution used in the process may be from about 0.01M to about 1M. Typically, the concentration of alkali solution is from about 0.02M to about 0.2M, more typically about 0.1M.

The quantity of alkali solution to chitosan may be in the range of from about 1 part chitosan to about 10 parts alkali solution up to about 10 parts chitosan to about 1 part alkali solution. Typically, the quantity of alkali solution to chitosan is about 1 part alkali solution to about 2 parts chitosan, more typically about 1 part alkali solution to about 1 part chitosan.

The alkali solution may comprise an alkali or alkaline earth component selected from the following, either alone or in combination: metal hydroxides, metal carbonates, metal bisulphites, metal persilicates, conjugate bases and ammonium hydroxide.

Suitable metals include sodium, potassium, calcium, or magnesium. Typically, the alkali component is sodium hydroxide, potassium hydroxide or sodium carbonate. Typically, sodium hydroxide is used.

Additionally, the final wound dressing composition of the invention may be washed to reduce the presence of endotoxins as described above. Typically, this washing step is carried out.

In each embodiment, the wound dressing composition is typically also sterilised prior to being packaged, in order that a physician can use the composition directly from its packaging.

The present invention also provides a method of absorbing a discharge of a fluid derived from a human or animal body, such as blood, and a method of stemming a flow of a fluid derived from a human or animal body from a physiological target site, comprising applying to the target site a wound dressing composition as described herein.

According to a further aspect of the invention, there is provided a method of maintaining the gel integrity for a period of at least about 24 hours of a wound dressing composition as described herein upon exposure to a fluid derived from a human or animal body.

According to a further aspect of the invention, there is provided a use of a wound dressing composition as described herein in absorbing a discharge of a bodily fluid from a physiological target site of a human or animal body, or of stemming a flow of a fluid discharged from a physiological target site a human or animal body.

The invention will now be described further by way of example with reference to the following examples which are intended to be illustrative only and in no way limiting upon the scope of the invention.

DETAILED DESCRIPTION

EXAMPLES

Method

In order to make a wound dressing composition according to the invention, the following procedure may be followed:
1. Chitosan fibres (which may or may not contain an antimicrobial agent, as desired) are carded into non-woven (50-300 gsm);
2. A solution of lactic acid, SDS, a Pluronic® poloxamer and a solvent (such as isopropyl alcohol) is prepared (Solution SLP);
3. Using a dip bath, spray system, or other, the Solution SLP is coated onto the chitosan non-woven and dried; and
4. The non-woven is then cut and packed and may be sterilised using gamma irradiation, or by treating the non-woven with ethylene oxide, the latter being preferred.

In order to evaluate the gel properties of the wound dressing composition, the composition has been tested in solutions which closely replicate the conditions of exposure to fluids from the human or animal body in which it would be used. As such, the wound dressing composition of the invention has been exposed to lysozyme solution, serum and simulated wound fluid. The simulated wound fluid contains 50% Fetal Bovine Serum and 50% Peptone water (0.9% NaCl+0.1% peptone in de-ionised $H_2O$).

Firstly, the wound dressing composition of the invention is immersed in a solution of each of lysozyme solution, serum and simulated wound fluid. In each case, the volume of the solution is greater than maximum absorbency of the composition.

The wound dressing composition and the solution is then sealed and incubated at 37° C.—i.e. body temperature—for a period of time for observation.

During this period, the formation of the gel upon the initial submersion is observed, and the gradual degradation of the composition and loss of gel integrity is visually assessed at numerous time points.

Analysis and experiments have shown that for samples containing 100% chitosan nonwoven plus differing levels of lactic acid provide a range of performance in SWF, when incubated at 37° C.

If the sample contains low levels of lactic acid, for example samples containing 12.5% add-on, the gel 'collapses' within 24 hours, e.g. the material changes from a gel presentation to a fabric, which is associated with a reduction in fluid retention (<70%).

If 25% lactic acid is added to a nonwoven, the material will form a gel (absorbence 30 g/cm$^2$, retention >80%), which will dissolve/degrade over a period of about 72 hours.

The presence of a supporting structure such as a viscose fibre, can prevent the complete dissolution of the sample; however a gel is not maintained. A chitosan/viscose nonwoven at low levels of lactic acid add-on (<25%) is associated with gel collapse, which is thought to be because the low lactic acid level has been utilized or sequestered by bioactives in the simulated wound fluid.

A chitosan/viscose nonwoven containing a higher level (>25%) of lactic acid is also associated with gel collapse, which is thought to be because the chitosan degrades, leaving the viscose fibres in situ without the gelling properties of the chitosan.

In accordance with the invention, with the addition of an anionic surfactant such as SDS and a poloxamer such as a Pluronic poloxamer (such as Poloxamer 188), it is possible to obtain a material that gels where the gel is maintained with acceptable levels of absorbance and retention over several days when incubated in simulated wound fluid at 37° C.

The gelling properties of such samples were evaluated by multiple assessors using a subjective scoring approach. A score of between 1 and 5 was given to samples following incubation in an excess of simulated wound fluid over multiple days at 37° C. The scoring approach is illustrated in Table 1 below.

TABLE 1

| Score | Appearance of Wound Dressing |
| --- | --- |
| 1 | Nonwoven Fabric feel |
| 2 | Some gel feel and appearance, poor retention, fibres observable |
| 3 | Gel feel and appearance, poor retention, fibres observable when compressed |
| 4 | Gel feel, good retention when compressed by finger, no fibres observed when compressed |
| 5 | Same as '4' except gel clarity greater. |

Samples of chitosan nonwoven to which 18.7% lactic acid, 2% SDS, and 2% Pluronic Poloxamer 188 had been added to, maintain a gel over multiple days; i.e. it is able to record a score of 5 at Day 0, and a score of 4 at Day 5. This formulation demonstrates excellent fluid handling properties in saline and simulated wound fluid; e.g. an absorbance under compression of 32 g/100 cm$^2$, and a level of fluid retention under compression of 85%.

Similarly, another formulation composed of chitosan nonwoven+21.7% lactic acid, 2.1% SDS, and 2.1% Poloxamer 188, maintains a gel over multiple days in SWF, recording a score of 4 at Day 5. It also demonstrates excellent fluid handling properties in saline and simulated wound fluid; e.g. an absorbance under compression of 35 g/100 cm$^2$, and a level of fluid retention under compression of 89%.

It can therefore be seen that the wound dressing compositions according to the invention maintains its gel integrity for a period that is greater than 24 hours, whereas those lacking the anionic surfactant and poloxamer do not.

It is of course to be understood that the present invention is not intended to be restricted to the foregoing examples which are described by way of example only.

The invention claimed is:

1. A wound dressing composition comprising:
   a chitosan, chitosan salt or chitosan derivative;
   an anionic surfactant selected from sodium dodecyl sulphate, ammonium lauryl sulphate, dioctyl sodium sulfosuccinate, potassium lauryl sulphate, sodium dodecylbenzenesulfonate, sodium laureth sulphate, sodium myreth sulphate, sodium pareth sulphate, and combinations of any two or more thereof; and
   a copolymer comprising a non-ionic triblock copolymer composed of a central hydrophobic chain of poly (propylene oxide) flanked by two hydrophilic chains of poly(ethylene oxide); and
   a physiologically acceptable acid in an amount of between 15% and 55% by weight of the wound dressing composition;
   wherein the wound dressing composition forms a gel upon contact with a fluid from a human or animal body, and is able to maintain gel integrity for at least about 24 hours.

2. A wound dressing composition according to claim 1, further comprising a copolymer comprising two or more homopolymer sub-units linked by covalent bonds.

3. A wound dressing composition according to claim 2, wherein the copolymer contains an approximate molecular mass of poly(propylene oxide) of from between 100 g/mol and 400 g/mol with a percentage poly(ethylene oxide) content of from about 10% to about 80%.

4. A wound dressing composition according to claim 3, wherein the copolymer contains an approximate molecular mass of poly(propylene oxide) of from between 150 g/mol and 250 g/mol with a percentage poly(ethylene oxide) content of from about 50% to about 80%.

5. A wound dressing composition according to claim 1, wherein the anionic surfactant and copolymer are each individually present in an amount of between about 0.01 and about 1.00% by weight of the wound dressing composition.

6. A wound dressing composition according to claim 1, wherein the copolymer is a poloxamer.

7. A wound dressing composition according to claim 6, wherein the poloxamer is selected from Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, and combinations of any two or more thereof.

8. A wound dressing composition according to claim 7, wherein the poloxamer comprises Poloxamer 188.

9. A wound dressing composition according to claim 1, wherein the anionic surfactant comprises sodium dodecyl sulphate.

10. A wound dressing composition according to claim 1, wherein the physiologically acceptable acid comprises an organic acid and/or an inorganic acid.

11. A wound dressing composition according to claim 1, wherein the organic acid is selected from formic acid, acetic acid, ascorbic acid, halogen acetic acids, propanoic acid, propenoic acid, lactic acid, succinic acid, acrylic acid, glyoxylic acid, pyruvic acid or a hydroxy propionic/butanoic acid, and combinations of any two or more thereof.

12. A wound dressing composition according to claim 1, wherein the organic acid is lactic acid.

13. A wound dressing composition according to claim 1, wherein the wound dressing composition is in the form of fibres.

14. A wound dressing compo tion according to claim 1, wherein the wound dressing composition comprises a chitosan salt.

15. A wound dressing composition according to claim 14, wherein the chitosan salt comprises one or more salts selected from chitosan acetate, chitosan lactate, chitosan succinate, chitosan malate, chitosan acrylate, chitosan formate, chitosan ascorbate, chitosan fluoroacetate, chitosan chloroacetate, chitosan propanoate, chitosan glyoxylate, chitosan pyruvate, chitosan sulphate, or chitosan chloride.

16. A wound dressing composition according to claim 15, wherein the chitosan salt comprises chitosan lactate.

17. A wound dressing composition according to claim 1, wherein the wound dressing composition comprises a chitosan salt, the anionic surfactant comprises sodium dodecyl sulphate, the poloxamer comprises a block copolymer comprising units of poly ethylene oxide) and poly(propylene oxide), the physiologically acceptable acid is lactic acid, and the wound dressing composition is in the form of fibres.

18. A wound dressing composition according to claim 1, wherein the molecular weight of the chitosan used for the preparation of the wound dressing composition is less than about 500,000.

19. A wound dressing composition according to claim 1, wherein the viscosity of the chitosan used for the preparation of the wound dressing composition is from about 40 to about 200 cps when measured at 20° C.

20. A wound dressing composition according to claim 1, wherein the wound dressing composition is sterilized.

21. A wound dressing composition according to claim 1, further comprising one or more components selected from pharmaceutical agents; wetting agents; colouring agents; processing aids; bulking agents; absorbent polymers; antimicrobial agents; growth factors; cytokines; agents which absorb agents which delay healing, and/or another wound dressing component.

22. A method of absorbing fluid discharged from a physiological target site of a human or animal body, or of stemming a flow of a fluid discharged from a physiological target site of a human or animal body, comprising applying to the physiological target site a wound dressing composition according to claim 1.

23. A wound dressing composition according to claim 15, wherein the chitosan salt comprises chitosan acetate.

24. A wound dressing composition according to claim 13, wherein the fibres are nano-fibres having a diameter of no more than about 100 microns and a length of no more than about 100 microns.

* * * * *